United States Patent [19]
Pilotti et al.

[11] Patent Number: 5,994,507
[45] Date of Patent: Nov. 30, 1999

[54] METHOD FOR BINDING ALBUMIN AND MEANS TO BE USED IN THE METHOD

[75] Inventors: Åke Pilotti, Täby; Tor Regberg, Stockholm; Christel Ellström, Uppsala; Charlotta Lindqvist, Uppsala; Ann Eckersten, Uppsala; Lars Fägerstam, Uppsala, all of Sweden

[73] Assignee: Amersham Pharmacia Biotech AB, Uppsala, Sweden

[21] Appl. No.: 09/001,940

[22] Filed: Dec. 31, 1997

[51] Int. Cl.$^6$ .......................... C07D 209/12; C07K 1/22; C07K 14/76; C08L 101/06

[52] U.S. Cl. .......................... 530/362; 525/50; 530/364; 564/180; 564/183; 564/184; 564/187; 546/146; 546/149; 546/323; 546/336; 546/337; 548/469; 548/492; 548/496; 548/537; 548/567; 549/72; 549/77; 549/487; 549/496

[58] Field of Search .................................. 530/362, 364, 530/366, 368, 413, 417; 525/50, 54.3; 210/692, 905; 564/180, 183, 184, 187; 549/72, 77, 487, 496; 546/146, 149, 323, 336, 337; 548/469, 492, 496, 537, 567

[56] References Cited

U.S. PATENT DOCUMENTS

| | | | |
|---|---|---|---|
| 4,981,961 | 1/1991 | Ngo | 536/112 |
| 5,656,729 | 8/1997 | Fuluhata et al. | 530/364 |

FOREIGN PATENT DOCUMENTS

97/39722  10/1997  WIPO .

OTHER PUBLICATIONS

Fisher et al, Dehydrophenylalanyl analogs of Bradykinin . . . Archives Biochem. Biophys. vol. 211, No. 1, pp. 269–275, Oct. 1, 1981.

*Primary Examiner*—Jeffrey E. Russel
*Attorney, Agent, or Firm*—Birch, Stewart, Kolasch & Birch, LLP

[57] ABSTRACT

A method for binding albumin by contacting an aqueous liquid containing an albumin with an albumin-binding compound is selected from albumin-binding compounds containing the scaffold —CO—NH—C(=C—)—CO—, and conjugates that are capable of binding albumin and exhibiting the scaffold —CO—NH—C(=C—)—CO—.

36 Claims, No Drawings

METHOD FOR BINDING ALBUMIN AND MEANS TO BE USED IN THE METHOD

BACKGROUND OF THE INVENTION

1. Field of the Invention

This invention concerns the use of a compound that is able to bind to albumin.

2. Description of the Related Arts

Albumin-binding ligands attached to a solid phase have been used for the removal of albumin from liquid samples mainly for two purposes: a) purification of albumin and b) further processing of the liquid samples in the absence of albumin. In order to obtain a sufficient quality of the final albumin preparation, the step involving binding to an albumin ligand has often been combined with other steps including ion exchange and binding based on hydrophobic interaction. Both batch-wise and chromatographic processes have been described.

Albumin-binding ligands in soluble form have been used for desorption of albumin adsorbed to a matrix via an albumin-binding ligand (e.g. regeneration of adsorbents). The soluble ligand then competes with the ligand covalently attached to the matrix for the same binding site on albumin.

Arrays of compounds and single compounds exhibiting scaffold I have been described in WO 9622529, WO 9400509 and WO 9401102. However, the possibility of finding efficient albumin-binding ligands among individual members of these previously described arrays has hitherto not been recognised.

SUMMARY OF THE INVENTION

There is a demand for improved albumin binders having affinities, selectivities and/or specificities better adapted to the above-mentioned processes. There is also a need to minimize the number of steps involved in the purification and removal of albumin from liquid samples.

There is also a need for separating albumins of different species from each other, for instance purifying human serum albumin from bovine serum albumin in the context of serum albumin produced by transgenic cows.

The present invention aims at providing solutions to these demands and needs.

A first aspect of the invention provides a method for binding albumin by contacting an aqueous liquid containing an albumin with an albumin binding compound which comprises the structure (scaffold)

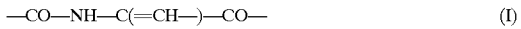
—CO—NH—C(=CH—)—CO—  (I)

The nature of the binding is unknown, but it is believed that ionic, hydrophobic, dipole-dipole interactions and other interactions of non-covalent nature may be involved including also hydrogen bonds and a good geometric fitness between the compound and the binding site on an albumin molecule. This type of ability to bind will be referred to as affinity.

As described below the scaffold may be part of a conjugate or a free compound. The use may be expressed as a method for binding albumin to an albumin-binding compound wherein the compound is selected from albumin-binding compounds containing the scaffold I.

A second aspect of the invention is novel conjugates that exhibit the scaffold I activity where the substituents at the free valencies in formula I are combined in a novel manner so as to optimize binding via affinity to an albumin.

By the term albumin is typically contemplated serum albumins from mammals and proteins having the analogous function in other vertebrates. The term albumin also encompasses albumin variants, such as genetically engineered forms, mutated forms, and fragments etc. having one or more binding sites that are analogous to a binding site unique for one or more vertebrate albumins as defined above. By analogous binding sites in the context of the invention are contemplated structures that are able to compete with each other for binding to one and the same ligand structure.

A low molecular weight (Mw) compound binding to one or more single binding sites on an albumin molecule through affinity will further on be called an albumin-binding ligand, or simply ligand. An albumin-binding ligand covalently attached to a carrier molecule gives an albumin-binding ligand-carrier conjugate, or simply a ligand-carrier conjugate or conjugate. The carrier molecule may also be called conjugated partner. Conjugates may contain one or more ligand structures binding to albumin. For a specific conjugate the Mw of the carrier is as a rule larger than the Mw of the scaffold I, i.e. larger than 96 dalton.

The term "albumin binders" is used generically to encompass albumin-binding ligands, albumin-binding ligand-carrier conjugates and other compounds exerting affinity to albumin.

DETAILED DESCRIPTION OF THE INVENTION

We have thus found that improved albumin binders may be found among compounds of formula II:

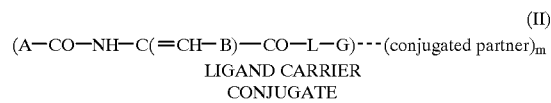

$$(A-CO-NH-C(=CH-B)-CO-L-G)\text{---}(\text{conjugated partner})_m \quad (II)$$
LIGAND CARRIER
CONJUGATE The configuration around —C=C— may be either Z or E, most likely with preference for the Z-isomer. The same applies also to Formula I. m is zero or 1. - - - represents that the conjugated partner is replacing a hydrogen in A, B, or -L-G. For m=0, the compound of formula II reduces to a ligand and for m=1 the compound is a conjugate. Determination of ability to bind albumin for a compound of formula II can be done as described below, but also prior art methods may be used.

The first aspect of the invention is a method for binding albumin by contacting a liquid medium containing albumin with an albumin binder under conditions permitting binding between albumin and the binder, wherein the binder is selected from among albumin binders comprising the scaffold —CO—NH—C(=CH—)—CO—, and particularly those fulfilling formula II.

This aspect of the invention may be used for the removal or purification of albumin from a liquid sample. A liquid sample containing albumin is contacted with a conjugate according to formula II in which m is equal to 1 and the conjugated partner is a carrier (matrix) that is soluble, insoluble or insolubilizable in aqueous liquid media.

In the case of purification of albumin, the matrix with bound albumin is separated from the liquid in a subsequent step and the bound albumin released, collected and further processed using methods that are known in the art. For insoluble carriers and insolubilizable carriers that have been made insoluble, the binding step is called adsorption and the release step desorption.

The release of albumin from the carrier may be performed according to general principles known in the art, e.g. with agents binding to the same site on albumin as the ligand or with an agent changing the site so as to render binding difficult or impossible. Soluble albumin-binding compounds of formula II, in particular where m=0, may act as powerful releasing agents. The conditions (pH, ionic strength, temperature, etc.) for adsorbing/desorbing should be non-denaturing for albumin with respect to irreversible denaturation in particular. Soluble carriers may be insolubilized after the binding step in order to facilitate physical separation of the complex between albumin and the ligand-carrier conjugate from the medium. Insolubilization steps typically take place before any release step.

Another aspect of the present invention is a method of obtaining samples that are free of one or more of the albumins mentioned above, for instance for the purification of compounds other than the typical albumins as defined above. Release and washing steps may be included as in conventional purification of albumins in order to be able to reuse the ligand-carrier material.

Removal of albumin according to the first aspect of the invention may be part of a chromatographic process utilizing as the conjugated partner an insoluble carrier in the form of a monolith or a population of particles/beads onto which surfaces an inventive albumin binder has been immobilized. Particles/beads may be in the form of a packed or fluidised bed. Fluidised beds may be stably expanded allowing chromatographic processes to take place. Particulate carriers may alternatively be used in batch-wise processes involving e.g. stirred suspensions.

The Ligand
Groups A and B

At two of the free valences in the scaffold (—CO—NH—C(=CH—)—CO—) there may typically be a group containing a 5- or 6-membered aromatic ring providing two or three double bonds conjugated to the carbonyl group, with preference for the left terminal carbonyl group, or carbon—carbon-double bond, respectively, of the scaffold I. The aromatic rings may comprise one, two or three heteroatoms providing at least one free electron pair and are selected from among oxygen, nitrogen or sulphur. The aromatic ring may be fused to other aromatic or non-aromatic rings each of which may have heteroatoms as discussed above. In Formula II, the two groups containing the aromatic rings are represented by parts A and B. These parts are often interchangeable.

The 5- or 6-membered aromatic ring may be represented by the formula:

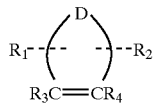

(III)

wherein - - - represents that $R_1$ and $R_2$ are substituting $R_3$, $R_4$ or a hydrogen in D.

The link from the aromatic ring to the scaffold I is through replacement of a hydrogen in D or of one of $R_1$ and $R_2$, or one of $R_3$ and $R_4$. A link to the scaffold I through replacement of one of $R_3$ and $R_4$ is only possible provided that $R_3$ and $R_4$ do not define a bivalent structure that is part of a ring fused to the aromatic ring of formula III.

D in formula III is selected from among —NH—CH=CH—, —CH=N—CH—, —NH—CH=N—, —NH—N=CH—, —N=N—NH—, —S—CH=CH—, —O—CH=CH—, —O—CH=N—, —S—CH=N—, —CH=CH—CH=CH—, —CH=CH—CH=N—, —CH=CH—N=CH—, —CH=CH—N=N—, —CH=NH—CH=N—, —N=CH—CH=N—, —N=CH—N=N—, and —N=CH—N=N—. These structural units may be inserted in either direction in formula III. Typically, the aromatic ring systems defined by formula III include phenyls, 1- and 2-naphthyls, 1- and 2-thienyls, 2-, 3- and 4-pyridyls, 2-, 3- and 4-quinolyls, 1-, 3- and 4-isoquinolyls, 2- and 3-indolyls, 2- and 3-furanyls, 1-, 2- and 3-pyrrolyls etc.

$R_1$ and $R_2$ may be selected from:
a. hydrogen (no replacement), alkyl, aryl, alkoxy, aryloxy and their thio analogues, typically a $C_{1-10}$ alkyl or $C_{5-15}$ aryl groups optionally substituted with one or more halo groups, e.g. $CF_3$—, $CH_3$—, phenyl etc;
b. halo, such as fluoro or chloro or bromo;
c. nitro;
d. cyano, carboxamido (—$CONH_2$) and carboxy (—COOH). Groups, such as N-substituted carboxamido (—$CONH_2$) with one or two amino hydrogens replaced with hydrocarbyl and hydrocarbyl esters and salts of carboxy, are included in carboxamido and carboxy, respectively. Typical hydrocarbyls are $C_{1-10}$ alkyl, such as arylalkyl or unsubstituted alkyl, or alkylaryl or unsubstituted aryl, for instance containing 5–15 carbons. Aryl groups may include phenyl, 1- and 2-naphthyls, 1-, 2- or 3-pyridyls etc. e. amino, such as primary, secondary and tertiary amino and corresponding ammonium groups and acylated and alkylated forms thereof including quaternary ammonium. Typical alkylated and acylated forms are those which are substituted with 1, 2 or 3 lower alkyls ($C_{1-12}$) or lower acyls ($C_{1-13}$), typically methyl or acetyl, respectively.

$R_3$ and $R_4$ may be hydrogen or together form a bivalent structure selected from among the D structures given above and in addition among —$CH_2$—S—$CH_2$—, —$CH_2$—O—$CH_2$—, —S—$CH_2$—$CH_2$—, —O—$CH_2$—$CH_2$—, —O—CH=CH—$CH_2$—, —$CH_2$—O—CH=CH—, —S—CH=CH—$CH_2$—, —$CH_2$—S—CH=CH—, —S—CH=CH—NH—, —$CH_2$—$CH_2$—$CH_2$—, —$CH_2$—$CH_2$—$CH_2$—, —$CH_2$—CH=CH—, —$CH_2$—CH=$CH_2$—, —$CH_2$—$CH_2$—CH=CH—.

Normal valence rules apply.

Group L-G

L is an organic structure linking the group G in formula II to the right carbonyl group in the scaffold (—CO—NH—C(=CH—)—CO—) as shown in formula II.

L is an organic structure, and may be —$(CH_2)_n(X)_m{}'(CH_2)_{n'}$— where the left and right free valences bind to the right carbonyl group of the scaffold and to the group G, respectively. X may be oxygen, sulphur or NH with the hydrogen preferably being replaced with a methyl group or a $C_{2-10}$ alkyl, n and n' are integers 0–3 and m' is an integer 0 or 1 with the proviso that n+n'+m' is 1, 2 or 3. One or more of the hydrogen atoms in a $CH_2$-group of the linker may be replaced with a $C_{1-10}$ alkyl group, or a hydroxy, a carboxy or an amino group or any other group containing a functional group enabling further derivatization and linking to a carrier.

The best affinities for albumin have so far been achieved for albumin binders in which X is NH with the hydrogen being replaced as suggested in the preceding paragraph and/or one or more of the $CH_2$-groups being substituted with a methyl and/or some other group as suggested in the preceding paragraph.

A preferred linker chain of the invention has substituents on the linker L so that rotation around bonds in the linker chain is hindered. Other means for hindering rotation in this part of the molecule may have similar effects on the affinity for albumin, for instance divalent groups bridging a position in L-G with a position in A or B or in the scaffold.

G is typically a hydrophobic group, such as a straight, branched or cyclic hydrocarbyl which possibly is substituted with, for instance, halo or hydroxy groups, etc. Typically G may be an aromatic group, such as phenyl, that may be substituted with a hydroxy and/or $C_{1-10}$ alkyl (e.g. methyl) in the ortho, meta or para position relative to the ring position binding to L.

The Conjugated Partner

In the conjugates of the present invention m is 1. The conjugated partner is linked to an albumin-binding ligand as defined in formula II via a bridge. The bridge may derive wholly or partly from the ligand or from the conjugated partner. For the sake of simplicity the bridge will be discussed as an inherent part of the conjugated partner, unless otherwise specified.

The conjugated partner itself may comprise additional albumin-binding ligands of the same or different structure as the ligand shown in formula II.

The conjugated partner may be attached to the ligand at a position in group A, B or L-G. It is preferred to have the conjugated partner attached (a) at a functional group in the linker L as suggested above, or (b) at the aromatic ring structures in either part A or part B so that the bridge attaching the conjugated partner to the ligand structure will contain a $sp^3$-hybridised carbon within two atoms distance from the aromatic ring. The bridge may thus have: —CH$_2$—CH$_2$—, —CH$_2$NH—, —NHCH$_2$—, —CH$_2$S—, —SCH$_2$—,—CH$_2$O—, or —OCH$_2$— next to the aromatic ring of part A or B.

The term "conjugate" in organic chemistry and biochemistry is well known and encompasses two or more compounds which are linked together covalently so that properties from each compound are retained in the conjugate. In the context of the present invention, the term conjugate means that an albumin-binding ligand as defined in formula II (m=0) is covalently linked (conjugated) to a compound (conjugated partner) that has a property that is retained in the conjugate. Typically the conjugated partner may render the conjugate soluble, insoluble or insolubilizable in the media concerned, analytically detectable, reactive against a specified target such as a biospecific counterpart etc.

The conjugated partner (carrier) may be insoluble, insolubilizable or soluble in the liquid media concerned. Typical media are aqueous, including water possibly containing water-miscible organic liquids, and other liquid media in which binding to albumin may take place. Typical carriers are based on organic or inorganic polymers which may be of synthetic or biological origin (biopolymers).

Insoluble carriers may be of the same kind as the carriers used as support in chromatography.

Suitable insoluble carriers may be of various physical forms such as monoliths, particles, tube walls etc. The carriers may be porous or non-porous.

The carrier may contain density controlling filler material (particles) embedded in a polymer.

Well known hydrophilic organic insoluble carriers are polymers which have on their liquid contact surface a plurality of hydrophilic groups, for instance hydroxy and/or amino and/or carboxy. Typical hydrophilic carriers are polyhydroxy polymers and polyamides, such as water-insoluble forms of polyvinyl alcohol, poly(hydroxyalkyl methacrylates) and corresponding acrylates, polyacryl- and polymethacrylamides (for instance trisacrylamides and trismethacrylamides (tris=(HOCH$_2$)$_3$CNH$_2$or (HOCH$_2$)$_3$CNH$_2$), polysaccharides, such as agarose, dextran, starch, pullulan, and cellulose, which possibly have been cross-linked in order to render them better adapted for use as adsorption/chromatography matrices. To this group of carrier belongs also hydrophobic carriers that have been hydrophilized (e.g. coated with a hydrophilic compound) on outer and inner (pore) surfaces.

Typical hydrophobic insoluble carriers are based on styrene-divinyl-benzene polymers, poly(alkyl methacrylates), polymers of perfluoro hydrocarbons (PFC) etc.

Inorganic variants of carriers may be based on materials such as glass, zeolites, silica, composites, zirconium oxide, etc.

Typical examples of carriers that are soluble in aqueous media as defined above are water soluble polymers, such as dextran.

The conjugated partner may contain an analytically detectable label, such as an enzymatically active moiety, a fluorophor/fluorogen and a chromophor/chromogen etc. a moiety giving the conjugate a predetermined reactivity, such as biotin, or a chemically reactive group. Analytically detectable conjugates may be useful in an assay such as immunoassay methods. Conjugates with a predetermined reactivity, such as biotin or a chemically reactive group will allow introduction of albumin-binding structures containing the scaffold I onto various types of other carriers, for instance for use in the above-mentioned methods for removal of albumin. These types of conjugated partners normally result in soluble conjugates.

Compounds of formula II may or may not bind to albumin. However, it is a routine matter to check for the albumin-binding capability of a certain compound. For instance, for quite a long time, there has been available a large number of well-characterized adsorbents with various ligand structures that provide affinity to albumin. In order to screen a large number of compounds and to optimize a certain general structure, albumin-binding experiments as outlined in the examples below are particularly useful. This screening method has enabled quick screening and optimization of compounds containing the inventive albumin-binding scaffold. A large number of albumin affinity compounds have been found. In principle any known method for checking affinity between two compounds may be modified and applied to screen for albumin-binding ligands. See for instance WO-A-9622530.

The conjugate of the second aspect of the invention has the formula (II):

(A—CO—NH—C(=CH—B)—CO—L—G) - - - (conjugated partner)   (II)

wherein A, B, and L-G, and - - - are as defined above. The conjugated partner is a polymeric carrier. The conjugated partner is linked to the ligand either at the A- or B-part or at L. The preferred variants are those that are preferred for use in the first aspect of the invention.

Synthesis Of Compounds of Formula II.

Compounds of formula II (m=0) may be synthesized starting from the appropriate oxazolone (unsubstituted at position 4) which is condensed with an aromatic aldehyde to substitute —CH$_2$— grouping in ring position 4 with a —C(=CH—Ar)— grouping where Ar is an aromatic group of the aromatic aldehyde. Subsequently the oxazolone ring is opened with an amine or an alcohol comprising structure G. The various steps utilized are described in WO-A-9400509, WO-A-9401102, WO-A-9518186, WO 9518627, WO 9518972, WO-A-9517903 and WO 9622529, which are incorporated by reference in their entirety.

See also in the Examples—Synthesis, which describes further the synthesis of compounds of formula (II).

EXAMPLES

Screening Method

In order to screen for albumin-binding ligands, a methodology using chromatography for indirect determination of ligand binding under non-equilibrium conditions is developed. Since non-equilibrium conditions are used, the kinetic rate constants of the interaction will have a pronounced effect on the binding 'signal' obtained. This is especially true for the dissociation rate constant which, if it differs for different ligand species with the same affinity for the target, will give different binding 'signal' amplitudes. A similar approach was used by Zuckermann et al (Proc. Natl. Acad. Sci. USA 89 (1992) 4505–4509) which is incorporated by reference herein.

The procedure comprises the steps:
1. Incubate target with ligand.
2. Separate target from free ligand.
3. Analyse target fraction for presence of ligand.

Standard Assay

The ligand to be assayed was dissolved in PBS and mixed with HSA dissolved in PBS (100 mM in HSA). The volume of the solution was selected so that the ratio between the ligand and HSA was 5:1 with final concentrations were for ligand 50 $\mu$M in 10 $\mu$M HSA (human serum albumin). The free ligand not bound to HSA was then removed by rapid passage through a HITRAP desalting column (SEPHADEX G25; Pharmacia Biotech AB, Uppsala, Sweden). The void fraction from the desalting column containing HSA and possible ligand complexed to HSA were collected and analysed by reverse phase chromatography (RPC) on HISEP 4.6/50 (SUPELCO, U.S.A.).

The result from the RPC step may be influenced by factors such as variation in ligand concentrations in the original ligand sample and differences in extinction coefficient for different ligands.

Instrumentation

Mixing step: GILSON 215 LIQUID HANDLER with a dilutor equipped with RACK 205 for deep well microtiter plates. RACK 202 for ELLERMAN tubes (KEBO, Sweden) equipped with a 1 ml dilutor syringe and a 1.5 ml transfer tubing.

Separation step: GILSON 215 LIQUID HANDLER with dilutor equipped with a RACK 202 for ELLERMAN tubes (KEBO, Sweden), a 1 ml dilutor syringe and a 1.5 ml transfer tubing, and a RHEODYNE fill port. FPLC System equipped with a HITRAP desalting column (SEPHADEX G25) (PHARMACIA BIOTECH AB, Uppsala). Sample dilution buffer and buffer A in FPLC: PBS (0.05 M Phosphate, 0.15 M NaCl, pH 7.0). Instant buffer for gel filtration (MIKROKEMI AB, Uppsala, Sweden). Buffer B in FPLC: Buffer A+20% (volume) acetonitrile. Buffer A was used for the gel filtration step and buffer B was used to regenerate the HITRAP column.

Analysis step: SMART System with m-Peak Monitor. GILSON 234 AUTOINJECTOR (the synchronization contact input was connected to the auxiliary output of the SMART). HISEP 4.6×50 mm column (SUPELCO, U.S.A). Eluent A: 180 mM ammonium acetate/acetonitrile (19:1 vol/vol). Eluent B: 180 mM ammonium acetate/acetonitrile (1:9 vol/vol)

Libraries and Screening Thereof.

Starting library: Construction and result of screening.

A screening library (Screening Library 1) was set up in order to screen for ligands that have affinity for IgG. No efficient IgG binding ligands were found. Since the library was at hand it was also checked for albumin binders.

Screening Library 1 was constructed from four different oxazolones:

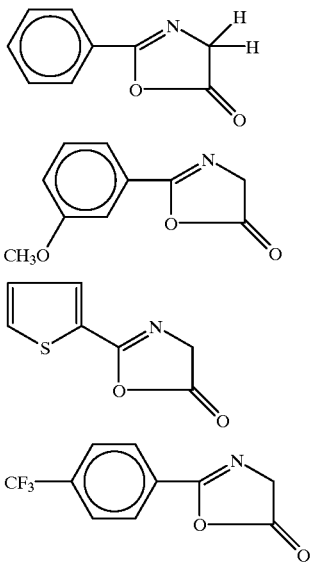

The oxazolones were condensed with 10 different heterocyclic aldehydes:

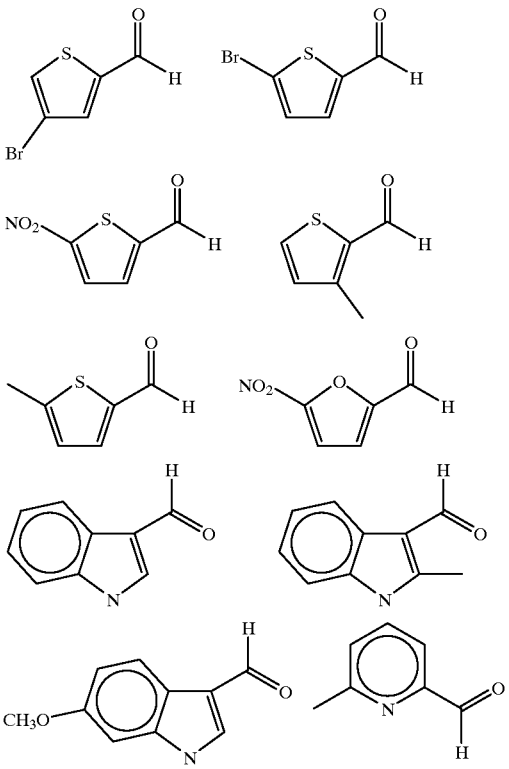

The obtained substituted oxazolones were subsequently opened with 40 different amines (Table 4):

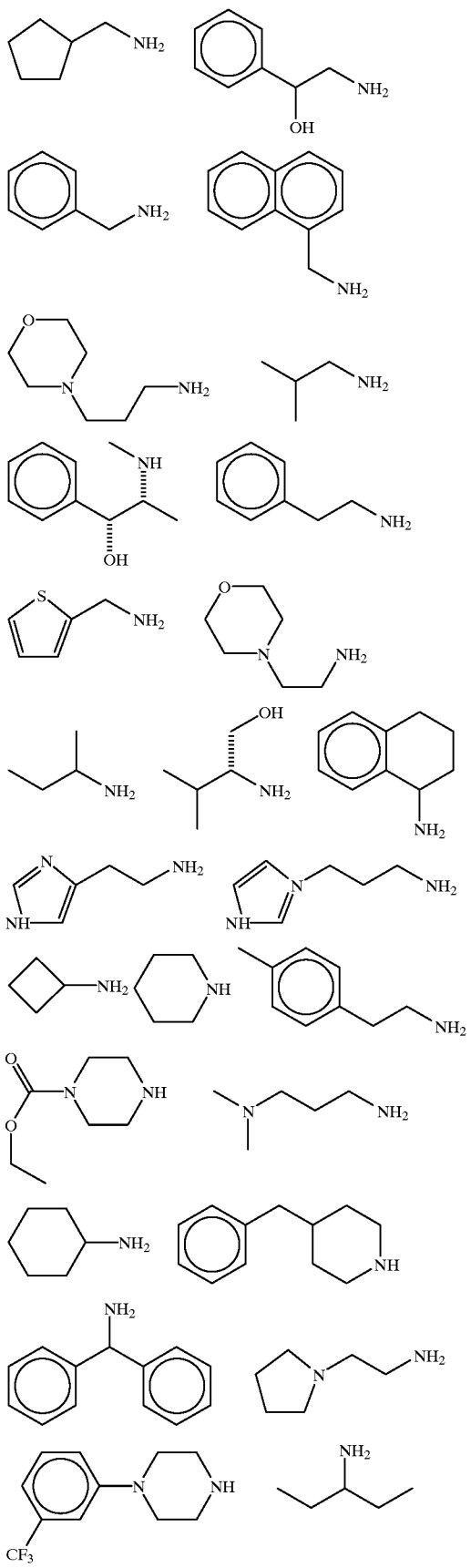
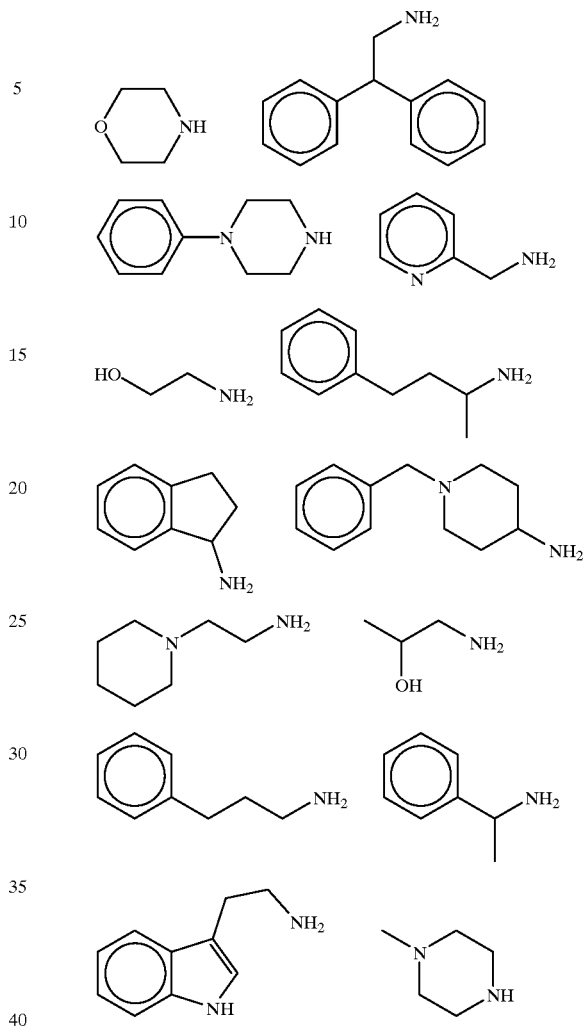

The products in the library array were not further purified. Final yields were typically around 80%. The crude products (ligand samples) thus sometimes consisted of a mixture of final and/or intermediate products and/or starting materials.

When the oxazolones were reacted with aldehydes, isomers differing in double bond configuration may be formed. The Z/E-ratio was typically 9:1, the stable Z isomer was the dominant one. This was confirmed by HPLC and $^1$H NMR. After the opening of the oxazolone with an amine the Z/E-ratio was still 9:1 (without working up). This ratio could be shifted, e.g. by the strong acidic/reductive conditions that was used to transform a nitro group in the A part into an amino group by reduction with tin chloride.

Screening the Screening Library 1 with human serum albumin (HSA) as the target substance resulted in hits for about 10% of the compounds tested. The affinity varied from weak to the extremely strong affinity found for Reference Compound 1 shown below, which is considered part of the present invention.

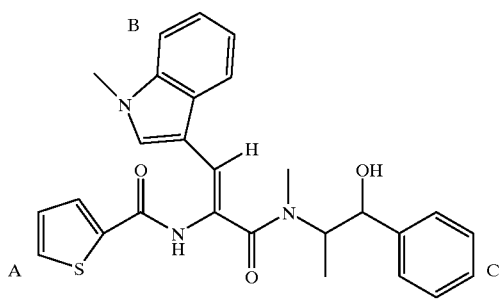

The library members that were positive for binding to HSA were also checked for binding to human IgG, lysozyme and human insulin. Reference compound 1 is compound 23 in Table 4.

Directed libraries and sublibraries were then constructed in order to map the Reference Compound 1-motif. Compounds containing handles and attachment points for carriers were synthesized based on similar conditions to those used for the synthesis of the original library. Examples—Synthesis.

Experiments in Connection with Reference Compound 1.

The particular ligand sample containing Reference Compound 1 was obtained by reaction of 3-(2-thienyl)-oxazolone with N-methyl-indole-3-aldehyde followed by subsequent ring-opening with ephedrine.

When the target substance (HSA=human serum albumin) and the ligand sample were mixed at equimolar concentration (10 mM) and applied directly to the RPC column, it was found that this ligand sample contained at least four different compounds, one of which showed reactivity towards HSA. The ligand sample as such was therefore subjected to preparative RPC and the four compounds were isolated and examined by mass spectrometry. It was determined that the molecular weight of the compound binding to HSA had a molecular weight of 473. In separate experiments two compounds with Mw 473, derivable from the reaction mixture and having NMR spectra suggesting they were the E and Z isomer, respectively were studied. Only Reference Compound 1 was active in binding to HSA. The results suggested that Z isomer was active in binding to albumin. No conclusive results have so far been obtained for the E-isomer.

Kinetic Dissociation Experiments with Reference Compound 1

By letting mixtures of HSA and Compound 1 pass the HITRAP column at different flow-rates (0.63 ml/min, 1.25 ml/min, 2.5 ml/min, 5 ml/min, 10 ml/min) the stability of the complex could be assessed which corresponds to dissociation times of 172 to 10.8 seconds.

After integration of the HSA and ligand peaks in the chromatograms, differences in the sample concentrations were corrected for by normalization of the HSA peaks. The ligand peak area as a function of dissociation time could be determined as shown by Table 1 below. By non-linear curve fitting, the data were interpreted to represent parallel and independent dissociation of ligand from two different binding sites on the HSA molecule according to:

$$[TL]_t = [TL(1)]_0 * e^{-kdiss1*t} + [TL(2)]_0 * e^{-kdiss2*t}$$

where TL(1) and TL(2) denote the two types of complexes with the apparent dissociation rate constants kdiss1 and kdiss2, respectively, and t denotes the time from start of dissociation.

TABLE 1

| t0 (s) | Area1 (AUmin) | kdiss1 ($s^{-1}$) | Area2 (AUmin) | kdiss2 ($s^{-1}$) |
|---|---|---|---|---|
| 10.8 | 8.09 | 2.19e-3 | 5.91 | 5.15e-2 |

Area1 and Area2 reflect the amount of ligand bound to the respective sites after 10.8 seconds (t0) of dissociation. By extrapolation to zero time the complex stoichiometry (at saturation) in the incubation mixture can be estimated. Standard curves for HSA and ligand were constructed and used to calculate the molar ratio which was found to be close to 2:1 (ligands/HSA).

AUmin stands for the integrated peak area in the chromatograms that form the basis for the kinetic study (absorbance units on the y-axis and time (minutes) on the x-axis).

Reference Library

AN1001 described in WO-A-9622529 was used as a reference library. It is an array based on oxazolones and contains 8000 compounds. It is a general library having members represented by formula II with known pharmacophore structures, usually aromatics, as groups A, B and L-G. Due to difficulties in solubilizing many of the members, it was never completely screened for albumin binders. The library was only used as a source for selecting interesting structures to be tested for binding to serum albumin.

RESULTS OF THE SCREENINGS

Variations in the A-group

The main objective of the synthetic design-work around the aromatic ring in the starting oxazolone (A-group) was to introduce a handle for attachment of the albumin ligand to a matrix. For the synthesis of different A-group analogues see Examples—Synthesis. A phenyl ring substituted with one or more of carboxylic acid function, amino, nitro, aminomethyl, chloromethyl, cyano and vinyl groups, for example, groups that either could be used directly for coupling or be converted to a coupling group were considered.

Vinylphenyl and chloromethylbenzyl oxazolones could not be used due to polymerization reactions. The cyanophenyl oxazolone derivative could be brought through the synthesis successfully, but the cyano group then could not be transformed into a carboxylic acid for later attachment to a matrix. These unsuccessful synthetic routes do not mean that the planned final product will bind to albumin.

The starting materials (A-, B- and L- G-group) for compounds that were synthesized with the goal to introduce a handle in the A-group are given in Table 2 which include compounds that have been tested for binding to serum albumin.

TABLE 2

Oxazolones with various handles in the A-part and different fused two-ring aromatic groups in the B-part.

| No | A-part | B-part | L-G from | Act. |
|---|---|---|---|---|
| 1 | 4-nitro-phenyl | N-methyl-indoly-3-yl | 1R,2S-(−)-ephedrine | + |
| 2 | 4-nitro-phenyl | Naphth-1-yl | 1R,2S-(−)-ephedrine | + |

TABLE 2-continued

Oxazolones with various handles in the A-part and different fused two-ring aromatic groups in the B-part.

| No | A-part | B-part | L-G from | Act. |
|---|---|---|---|---|
| 3 | 4-nitro-phenyl | Naphth-1-yl | 1R,2S-(−)-ephedrine | I |
| 4 | 4-nitro-phenyl | Quinolin-4-yl | 1R,2S-(−)-ephedrine | − |
| 5 | 4-amino-phenyl | N-methyl-indoly-3-yl | 1R,2S-(−)-ephedrine | (+) |
| 6 | 4-amino-phenyl | N-methyl-indoly-3-yl | 1R,2S-(−)-ephedrine | (+) |
| 7 | 4-amino-phenyl | Quinolin-4-yl | 1R,2S-(−)-ephedrine | (+) |
| 8 | 4-amino-phenyl | Naphth-1-yl | 1R,2S-(−)-ephedrine | + |
| 9 | 4-amino-phenyl | Naphth-1-yl | 1R,2S-(−)-ephedrine | (+) |
| 10 | 4-cyano-phenyl | Naphth-1-yl | 1R,2S-(−)-ephedrine | (+) |
| 11 | 4-(NH$_2$CO-)-phenyl | Naphth-1-yl | 1R,2S-(−)-ephedrine | (+) |
| 12 | 4-(benzyl-OCONHCH$_2$)-phenyl | Naphth-1-yl | 1R,2S-(−)-ephedrine | I |
| 13 | 4-(aminomethyl)-phenyl | Naphth-1-yl | 1R,2S-(−)-ephedrine | − |
| 14 | 4-(CH$_3$CO—NHCH$_2$)-phenyl | Naphth-1-yl | 1R,2S-(−)-ephedrine | + |

Compounds 2 and 3 are isomers.
"+" represents strong binding, "(+)" weak binding and "−" no binding.
"X" represents the link to the scaffold. "Act" is activity and "I" is insoluble.

For details on synthesis see Examples—Synthesis. The results of the testing for affinity to albumin are apparent from Table 2. All of the amino-substituted phenyloxazolones were more or less active, while the nitro-, cyano-, amide-substituted compounds differed in activity.

Coupling of active compounds at functional groups directly attached to the phenyl ring (A-group) to insoluble carriers gave conjugates that were more or less inactive in binding to albumin. Conjugates that were active in binding to albumin were obtained in the case of a methylene group was inserted between the functional group used for attachment of the conjugated partner and the aromatic ring of the A-group. The rationale for this may be that a methylene group and other chains comprising sp$^3$-hybridized atoms at this position make the linkage between the ligand structure and the conjugated partner more flexible and facilitates rotation.

Variations in the B-part

The screening of Library 1 and selection of compounds from the reference library gave insight to the requirements for this part. It appeared favourable with structures such as fluoro containing single aromatic rings, fused two-ring systems and also pyridine rings.

The syntheses to introduce a handle on the B-part was restricted to indoles. N-allyl-indole-3-aldehyde and N-chlorobutylindole-3-aldehyde were synthesized. Some of the starting indoles also exhibited methyl substituents at various positions. Tested compounds are given in Table 3.

TABLE 3

Variations in the B-part.

| No | A-part | B-part | L-G from | Act. |
|---|---|---|---|---|
| 15 | thiophen-2-yl | N-allyl-indol-3-yl | 1R,2S-(−)-ephedrine | + |
| 16 | thiophen-2-yl | N-(4-chlorobutyl)-indol-3-yl | 1R,2S-(−)-ephedrine | (+) dil 1 + 3 |

I, Act, X, (+), + and − have the same meaning as in Table 2.

The rules for the B-part retaining affinity to albumin when linking an active albumin-binding ligand to a conjugated partner should be similar to the rules for the A-part.

Variations in the L-G-part

From the screening of Library I against serum albumin and some other proteins it was concluded that the L-G part, in particular the ephedrine part, was important for high activity and selectivity for serum albumin. Low binding activity could be obtained for other groups, primarily those originating from oxazolone ring opening with hydrophobic amines (R—NH$_2$ where R may be an hydrocarbyl group, such as aryl or alkyl group). It is likely that this effect is retained even if the hydrocarbyl group has one or more smaller hydrophilic groups that do not completely overcome the hydrophobicity. Only ligands with L-G-parts deriving from ephedrine were therefore selected, when ligands from the reference library were selected for testing.

Most of the synthetic work was focused on the L-G-part of the molecule. Various L-G-part analogues of Reference Compound 1 were prepared from ephedrine and norephedrine (which is missing the N-methyl group) and some other ephedrine analogues:

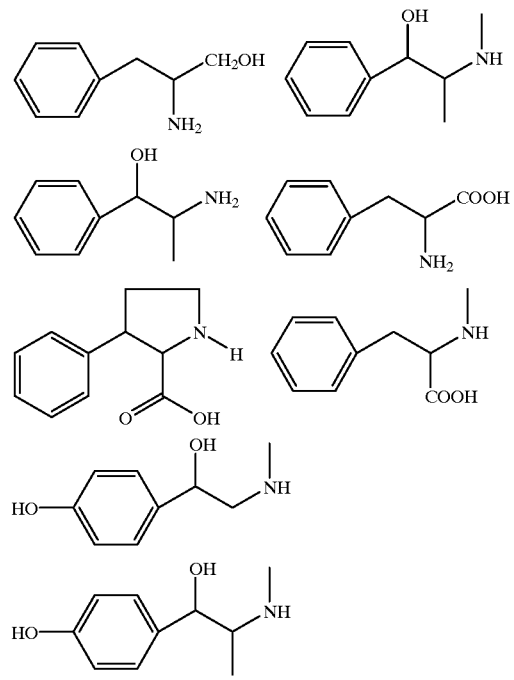

The results for ephedrine analogues are given in Tables 4 and 5.

TABLE 4

Result in activity for the products from reaction of 1-methylindole-3-thienyloxazolone with different amines.

| No. | L-G from | Solvent | Triethylamine | Temp | Act. |
|---|---|---|---|---|---|
| 17 | 1R,2S-(−)-1-phenyl-1-hydroxy-2-amino-propane | THF | | 55° C. | − |
| 18 | L-1-phenyl-2-amino-3-hydroxy-propane | THF | | 55° C. | (+) |
| 19 | D-1-phenyl-2-amino-3-hydroxy-propane | THF | | 55° C. | (+) |
| 20 | 1S,2R-(+)-ephedrine | THF | | 55° C. | + |
| 21 | 1S,2S-(+)-ephedrine | THF | | 55° C. | + |
| 22 | 1S,2R-(+)-1-phenyl-1-hydroxy-2-amino-propane | THF | | 55° C. | + |
| 23 | 1R,2S-(−)-ephedrine | THF | | 55° C. | + |
| 24 | L-phenylalanine | ACN/ H$_2$O (5:2) | 2.4 eq | 70° C. | − |
| 25 | S,3R-3-phenyl-pyrrolidine-2-carboxylic acid | ACN/ H$_2$O (5:2) | 2.4 eq | 70° C. | − |
| 26 | N-methyl-L-phenylalanine | ACN/ H$_2$O (5:2) | 2.4 eq | 70° C. | + |
| 27 | N-methyl-D-phenylalanine | ACN/ H$_2$O (5:2) | 2.4 eq | 70° C. | + |

I, Act, X, (+), + and − have the same meaning as in Table 2.

TABLE 5

Activity for compounds obtained by ring-opening where the opening of the oxazolones has been done with different amines.

| No | A-part | B-part | L-G- from | Reaction conditions | Act. |
|---|---|---|---|---|---|
| 28 | thiophen-2-yl | naphth-1-yl | 1S,2S-(+)-ephedrine | 55° C. THF | I |
| 29 | thiophen-2-yl | naphth-1-yl | 1S,2R-(+)-norephedrine | 55° C. THF | (+) Dil 1+1 |
| 30 | thiophen-2-yl | naphth-1-yl | 1R,2S-(−)-ephedrine | 55° C. THF | I |
| 31 | thiophen-2-yl | naphth-1-yl | N-methyl-L-phenylalanine | ACN/ H$_2$O (3:1), 2.3 eq TEA, 70° C. | − |
| 32 | thiophen-2-yl | naphth-1-yl | N-methyl-D-phenylalanine | ACN/ H$_2$O (3:1), 2.3 eq TEA, 70° C. | (+) |
| 33 | phenyl | naphth-1-yl | 1S,2S-(+)-ephedrine | 55° C. THF | I |
| 34 | phenyl | naphth-1-yl | 1S,2R-(+)-norephedrine | 55° C. THF | − |
| 35 | phenyl | naphth-1-yl | 1R,2S-(−)-ephedrine | 55° C. THF | (+) dil 1+1 |
| 36 | phenyl | naphth-1-yl | N-methyl-L-phenylalanine | ACN/ H$_2$O (3:1), 2.3 eq TEA, 70° C. | − |
| 37 | phenyl | naphth-1-yl | N-methyl-D-phenylalanine | ACN/ H$_2$O (3:1), 2.3 eq TEA, 70° C. | (+) |
| 38 | phenyl | N-methyl-indol-3-yl | 1S,2S-(+)-ephedrine | 55° C. THF | I |
| 39 | phenyl | N-methyl-indol-3-yl | 1S,2R-(+)-norephedrine | 55° C. THF | − |
| 40 | phenyl | N-methyl-indol-3-yl | 1R,2S-(−)-ephedrine | 55° C. THF | + |
| 41 | phenyl | N-methyl-indol-3-yl | N-methyl-L-phenylalanine | ACN/ H$_2$O (3:1), 2.3 eq TEA, 70° C. | (+) |
| 42 | phenyl | N-methyl-indol-3-yl | N-methyl-D-phenylalanine | ACN/ H$_2$O (3:1), 2.3 eq TEA, 70° C. | (+) |
| 43 | thiophen-2-yl | N-methyl-indol-3-yl | (±)-synephrine | THF/ACN (1:1), 70° C. | − |
| 44 | thiophen-2-yl | N-methyl-indol-3-yl | L-phenylalanine | ACN/ H$_2$O (7:1), 2.3 eq TEA, 70° C. | − |
| 45 | thiophen-2-yl | N-methyl-indol-3-yl | N-methyl-L-phenylalanine | ACN/ H$_2$O (3:1), 2.3 eq TEA, 55° C. | (+) |
| 46 | thiophen-2-yl | N-methyl-indol-3-yl | N-methyl-D-phenylalanine | ACN/ H$_2$O (3:1), 2.3 eq TEA, 55° C. | (+) |
| 47 | thiophen-2-yl | N-methyl-indol-3-yl | p-hydroxyephedrine hydrochloride | ACN/ H$_2$O (4:1), 1 eq TEA, 55° C. | − |

I, Act, X, (+), + and − have the same meaning as in Table 2.

The results presented in Table 4 illustrate that the albumin-binding activity may be enhanced if L contains a group that can stabilize the conformation by the introduction of a rotational barrier around the nitrogen and the C1 carbon in ephedrine (in this case a methyl that is γ to the phenyl ring). The finding that a functional group permitting coupling to a conjugated partner could be introduced in the L-G-part was important (N-methyl-phenyl alanine).

The results presented in Table 5 illustrate that phenyl- and thienyl oxazolones and indolyl and naphthyl aldehydes can be used to introduce parts A and B, respectively, in the case where the L-G-part derives from ephedrine analogues. Solubility problems appeared when the groups in the A- and the B-part are too hydrophobic.

Binding Specificity

Reference Compound 1 and its N-methyl alanine D and L analogues A3 and B3, respectively:

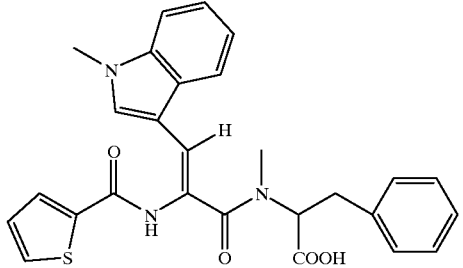

were tested under ordinary screening conditions for binding to HSA, lysozyme, IgG and insulin in order to test the specificity for serum albumin. Except for HSA, none of the proteins bound to these ligands. Binding of serum albumin from other species was also tested. The results in the latter case were non-conclusive leaving the question open if the novel albumin binders comprise ligands that will discriminate between, for instance, bovine and human serum albumins.

Reference library: Tested compounds that have affinity to serum albumin

L-G-part derived from ring opening with ephedrine. For the below groups A, group B were:

A=phenyl: B=3-trifluoromethyl phenyl, 4-trifluoromethyl phenyl, 1-naphtyl.

A=3-methoxy phenyl: 2,4-difluoro phenyl, 2-fluoro phenyl, 3-fluoro phenyl, 4-trifluoromethyl phenyl, 2-methyl phenyl, 3-pyridyl, 2-pyridyl.

A=2-naphthyl: 2,4-difluoro phenyl, 3-fluoro phenyl, 4-fluoro phenyl, 2-methyl phenyl.

A=2-thienyl: 3-fluoro phenyl, 4-fluoro phenyl, 1-naphthyl.

A=4-trifluoromethyl phenyl: 2,4-difluoro phenyl, 3-fluoro phenyl, 4-fluoro phenyl, 2-methyl phenyl, 3-chloro phenyl, 3-pyridyl, 4-pyridyl, 4-chloro phenyl, 3-quinolyl.

A=2,4-dichloro phenyl: 2,4-difluoro phenyl, 2-fluoro phenyl, 2-trifluoromethyl phenyl, 3-trifluoromethyl phenyl, 2-methyl phenyl, 4-methioxy-phenyl, 4-phenyl phenyl, 1-naphthyl, 3,5-difluoro phenyl, 4-pyridyl, 3-quinolyl.

A=4-methyl phenyl: 2-fluoro phenyl, 2-methyl phenyl, 4-methioxy phenyl, 3,5-difluoro phenyl.

A=3-methyl phenyl: 3-fluoro phenyl, 4-fluoro phenyl, 2-trifluoromethyl phenyl, 1-naphthyl, 4-trifluoromethoxy phenyl, 3-phenoxy phenyl.

Methods and Analyses

The characterization was performed on a JEOL ECLIPSE-270 MHz NMR. The samples were run in 5 mm:s probes and the substances were dissolved in $CDCl_3$ or $DMSO-d_6$. TMS was used as an internal standard. TLC was run on MERCK KIESELGEL $F_{254}$ and was eluted with ethylacetate and then developed under UV-light (254 nm). HPLC was performed on a SMART System on a SUPELCO HISEP column.

References

1. Y. S. Rao and R. Filler, Geometric Isomers of 2-Aryl (Aralkyl)-4-arylidene(alkylidene)-5(4H)-oxazolones, Synthesis 749–764, 1975, incorporated by reference herein in its entirety.

EXAMPLE—SYNTHESIS

In each of the examples 1–8 presented below, factors such as solvents, temperatures, order of additions, reaction times and working up protocols, etc. were selected so as to fit the reactants used. $^1$H NMR, MS and HPLC results provide support that the desired compounds had been obtained. If needed also other criteria for checking the outcome of the individual reactions were employed.

Example 1

Compounds of Formula II with A=thien-2-yl; B=1-methyl-indol-3-yl, 1-allyl-2-methyl-indol-3-yl, naphth-1-yl or 1-(4-chlorobut-1-yl)-indol-3-yl A. Synthesis of the starting oxazolone.

N-thiophene-2-carboxamide glycine: In a 1000 ml 3-necked reaction flask 77.0 g glycine was dissolved in 600 ml water with a mechanical stirrer. NaOH (12.0 g) was added to form sodium glycinate. The reaction mixture was then cooled to 5° C. Thiophene carbonyl chloride was added dropwise and conc. NaOH-solution (50%) was periodically added to keep pH around 10 during 1.5 h. The temperature rised to 12° C. during the addition and the solution became homogeneous. After another hour conc. HCl (70 ml) acidified the mixture to pH 2 and the stirring continued for two hours. The precipitated crystals were filtered off and washed with water. The product was confirmed with NMR after drying in a vacuum oven at 60° C. $^1$H NMR shifts: δ=4.05 (s, 2H), δ=7.12 (dd, 1H), δ=7.65 (dd, 1H), δ=7.71 (dd, 1H). Yield: 90–100% (ca.130 g).

2-(Thien-2-yl)-oxazolone: In a 2L 3-necked flask with mechanical stirrer 66.8 g dicyclohexylcarbodiimide (DCC) was dissolved in 100 ml anhydrous THF. Thiophene-2-carboxamideglycine dissolved in 600 ml anhydrous THF was added dropwise during 30 min. The reaction mixture was then allowed to stir for 24 hours at room temperature. The mixture was cooled to 5° C. and dicyclohexylurea was filtered off. After evaporation of THF the solid product was dissolved in hot dichloromethane and then cooled so that more dicyclohexylurea could be filtered off. The solution was evaporated and chromatographed on 400 g silica through a 15 cm wide column with dichloromethane. The first 3L was collected and evaporated to give 19 g product. $^1$H NMR shifts: δ=7.14 (dd, 1H), δ=7.59 (dd, 1H), δ=7.7ppm (dd, 1H). Yield: 35% (19g).

B1. Introduction of 1-methyl-indol-3-yl as ring system B.

2-(thien-2-yl)-oxazolone 3.0 g (18 mmol) was mixed with 2.0 g (12.6 mmol) 1-methylindole-3-aldehyde in 12 ml toluene in a screw-cap tube. Triethylamine (0.8 ml) was added and the closed tube placed on a heating block at 70° C. over night. The dark red-brown reaction mixture, with crystals in, diluted with 200 ml toluene and acetone, then extracted with 3×100 ml water. The toluene layer was dried with $MgSO_4$, evaporated to 20 ml and then crystals fell over night and these were dried in a vacuum-oven at 60° C. 1H NMR showed that some starting material was still present. The product was recrystallized from toluene and H NMR confirmed the product. $^1$H NMR shifts: δ=3.93 (s, 3H), δ=7.17 (dd, 1H), δ=7.3–7.4 (m, 3H), δ=7.60 (dd, 1H), δ=7.62 (s, 1H), δ=7.81 (dd, 1H), δ=7.95 (d, 1H), δ=8.42 (s, 1H). Yield: 23% (0.89g).

B2. Introduction of naphth-1-yl as ring system B.

2-(thien-2-yl)-oxazolone 2.5 g (15 mmol) was mixed with 2.3 g (15 mmol) naphthalene-1-aldehyde in 12 ml toluene in a screw-cap tube. Triethylamine (1.0 ml) was added and the closed tube placed on a heating block at 70° C. over night (17 h). The precipitated crystals were dissolved in 100 ml toluene and 50 ml acetone and the mixture was heated until all was in solution. After crystals had fallen and been collected, a $^1$H NMR spectrum was run which showed that some starting material was left. After recrystallization in toluene, $^1$H NMR confirmed the pure product. $^1$H NMR shifts: δ=7.21 (dd, 1H), δ=7.40–7.66 (m, 4H) δ=7.69 (dd, 1H), δ=7.90 (d, 1H), δ=7.92 (dd, 1H), δ=7.97 (d, 1H), δ=8.08 (s,1H), δ=8.30 (d,1H), δ=8.97 (d,1H). Yield: 18% (0.83 g)

B3. Introduction of 1-allyl-2-methyl-indol-3-yl as ring system B.

1. Synthesis of N-allyl-2-methyl-indole-3-aldehyde.

2-Methyl-indole-3-aldehyde (3.18 g, 20 mmol) and KOH (1 g) dissolved in 15 ml DMSO was added dropwise to allylbromide (2.6 ml, 30 mmol) dissolved in 5 ml DMSO at 60° C. and stirring. A saturated aqueous solution of KOH was added during the reaction to keep the pH 10–11. Totally about 4 ml KOH-solution was added. The reaction mixture was partitioned between toluene and water. The toluene-layer was carefully extracted with water several times. The organic phase was evaporated to an oil containing DMSO. It was extracted again between diethyl ether/toluene and water, and the organic phase evaporated to give an oil. When 5ml diethyl ether was added crystallization took place immediately. After the crystals were filtered and washed with diethyl ether/hexane they were recrystallized from 25 ml diethyl ether. TLC in toluene/EtOAc (1:1) showed approximately 95% purity and $^1$H NMR confirmed the product. $^1$H NMR shifts: δ=2.64 (s, 3H), δ=4.71 (d, 1H), δ=5.17 (d, 1H), δ=5.85 (d, 1H), δ=5.90 (m,1H), δ=7.25 (m, 3H), δ=8.27 (d, 1H), δ=10.18 (s,1H=aldehyde). Yield: 58% 2.3 g).

2. Introduction of 1-allyl-2-methyl-indol-3-yl as ring system B. 2-(thien-2-yl)oxazolone (400 mg, 2.4 mmol) and 1-allyl-2-methyl-indole-3-aldehyde (477 mg, 2.4 mmol) were dissolved in 2.5 ml toluene in a screw-cap tube. Triethylamine (163 μl, 2.4 mmol) was added and the closed tube placed on a heating block at 70° C. over night (17 h). When the tube cooled; crystals were formed and these were collected and washed with cold toluene. The crystals were then recrystallized two times from toluene and after drying in a vacuum oven at 60° C., $^1$H NMR confirmed the product. $^1$H NMR shifts: δ=2.61 (s, 3H), δ=4.75 (d, 2H), δ=4.88 (dd,1H), δ=5.20 (dd, 1H), δ=5.93 (m, 1H), δ=7.25–7.36 (m, 3H), δ=7.51 (s, 1H), δ=7.57 (dd, 1H), δ=7.79 (dd, 1H), δ=9.18 (d,1H). Yield: 13% (110 mg).

B4. Introduction of 1-(4-chlorobut-1-yl)-indol-3-yl as ring structure B.

1. Synthesis of 1-(4-chlorobut-1-yl)-indole-3-aldehyde.

Indole-3-aldehyde (1.45 g, 10 mmol) was dissolved in 5.0 ml dry DMSO, and KOH (0.5 g) was added. 1-bromo-4-chlorobutane (2.57 g, 15 mmol), dissolved in 3 ml DMSO, was added in 3 portions during 3 h. The reaction was shaken at 60° C. At each addition of 1-bromo-4-chlorobutane, 0.5 ml 45° C. KOH was added (totally 1.5 ml). After the reaction was completed the reaction mixture was extracted with H$_2$O/toluene several times. The organic phase was evaporated to yield an oil which was dissolved in diethyl ether (45 ml) and kept at −20° C. for 3 days. The solid was filtered off and washed with ether and dried. Yield: 76%=1.8 g. TLC showed a very small spot of impurity (ca 10%), possibly the C-2 chlorobutane derivative. Due to this, the product was recrystallized from diethyl ether with a small volume of acetone (total volume ca 10 ml). The products cocrystallized so a short silica column was run and the products eluted with toluene/EtOAc 2:1 to give pure compound. $^1$H NMR shifts: δ=1.80 (q, 2H), δ=2.07 (q, 2H), δ=3.53 (t, 2H), δ=4.20 (t, 2H), δ=7.25–7.35 (m, 3H), δ=7.70 (s, 1H), δ=8.30 (d, 1H), δ=9.99 (s, 1H).

2. Introduction of ring structure B. 2-(thien-2-yl)-oxazolone (500 mg, 3 mmol) and N-(4-chlorobutane)indole-3-aldehyde (700 mg, 3 mmol) were dissolved in 3ml toluene in a screw-cap tube. Triethylamine (200 μl, 3 mmol) was added and the closed tube placed on a shaking heating block at 70° C. over night (17 h). The reaction mixture was dissolved in 10 ml toluene and 5 ml acetone and extracted with 3×10 ml water. The toluene phase was dried with MgSO$_4$ and evaporated. A short silica column was run and the products eluted with toluene/EtOAc 9:1 to give a pure compound. $^1$H NMR shifts: δ=1.86 (q, 2H), δ=2.13 (q, 2H), δ=3.57 (t, 2H), δ=4.29 (t, 2H), δ=7.13–7.22 (m+dd, 1+1H), δ=7.29–7.41 (m, 3H), δ=7.60 (dd, 1H), δ=7.61 (s, 1H), δ=7.82 (dd, 1H), δ=7.95 (m, 1H), δ=8.42 (s, 1H). Yield: 24% (280 mg).

C. Reaction of oxazolones with amines (introduction of ring structure C (i.e. -L-G)).

The oxazolone is mixed with the amine and the solvent in a screw-cap tube. The tube is placed on a heating block over night (18 h) and then the solvent is evaporated with heat and/or nitrogen. The synthetic products were not purified further, but used as they were. The raw products were analyzed with HPLC, TLC and some of them with $^1$H NMR and ESMS and found to agree with the expected compounds. The amines used are given above under the heading "Variations in the L-G-part". The solvent, temperature and addition of triethyl amine are provided in Tables 4–5.

Example 2

Compounds of formula II with A=Phenyl; B=1-methyl-indol-3-yl or naphth-1-yl

A1. Introduction of 1-methyl-indol-3-yl as ring system B. 2-phenyloxazolone 5 g (31 mmol) was dissolved with 4.93 g (31 mmol) 1-methylindol-3-aldehyde in 30 ml toluene in a screw-cap tube. Triethylamine (2.0 ml) was added and the closed tube placed on a heating block at 70° C. over night (17 h). The precipitated crystals were dissolved in 200 ml toluene and 100 ml acetone and the mixture was heated until all was in solution. After crystals had fallen and been collected, a $^1$H NMR spectrum was run which showed that some starting material was left. After recrystallization from toluene, $^1$H NMR confirmed the pure product. $^1$H NMR shifts: δ=3.95 (s, 3H), δ=7.30–7.40 (m, 3H), δ=7.47–7.58 (m, 3H), δ=7.65 (s, 1H), δ=7.99 (dd,1H), δ=8.15 (dd, 2H), δ=8.45 (s, 1H). Yield: 37% (3.46 g).

A2. Introduction of naphth-1-yl as ring structure B.

2-Phenyloxazolone 2.5 g (16 mmol) was dissolved together with 2.42 g (16 mmol) 1-naphthaldehyde in 15 ml toluene in a screw-cap tube. Triethylamine (1.0 ml) was added and the closed tube placed on a heating block at 70° C. over night (17 h) The solvent was evaporated with heat and nitrogen and the reaction mixture was dissolved in hot ethyl acetate and a few drops of methanol and then cooled. The crystals that grew from the solution were characterized to be the product by $^1$H NMR. $^1$H NMR shifts: δ=7.50–7.68 (m, 6H), δ=7.90 (d,1H), δ=7.97 (d, 1H), δ=8.14 (s,1H), δ=8.21 (dd, 2H), δ=8.31 (d, 1H), δ=9.2 (d, 1H). Yield: 34% (1.64 g).

B. Reaction of oxazolones with amines (introduction of ring structure G (i.e. -L-G)).

The oxazolone is mixed with the amine and the solvent in a screw-cap tube. The tube is placed on a heating block over night (18 h) and then the solvent is evaporated with heat and/or nitrogen. The synthesized products were not purified further, but used as they were. The raw products were analyzed with HPLC, TLC and some of them with $^1$H NMR and ESMS. The amines used are provided above, under the heading "Variations in the L-G-part". The solvent, temperature and addition of triethyl amine are given in Tables 4–5.

Example 3

Compounds of formula II with A=4-nitro-phenyl; B=1-methylindol-3-yl or quinol-4-yl; -L-G deriving from (−)-(1R, 2S)-ephedrin.

Solvents, temperature, order of addition, reaction times and working up protocol were selected so as to fit the reactants used. $^1$H NMR, MS, HPLC results provided support that the desired compounds had been obtained.

A. 2-(4-nitro-phenyl)oxazolones. This compound was prepared by acetic anhydride cyclization of 4-nitrohippuric acid.

B1.Introduction of 1-methylindol-3-yl as ring system B and of structure -L-G by oxazolone ring opening with (−)-(1R, 2S)-ephedrine. These two steps were carried out as described above for other oxazolones, aldehydes and amines, the aldehyde now being 1-methylindol-3-aldehyde.

B2.Introduction of naphth-1-yl as ring system B of structure -L-G by oxazolone ring opening with (−)-(1R, 2S)-ephedrine. These two steps were carried out as described above for other oxazolones, aldehydes and amines, the aldehyde now being naphthalene-1-aldehyde.

B3.Introduction of quinol-4-yl as ring system B and of structure -L-G by oxazolone ring opening with (−)-(1R, 2S)-ephedrine. These two steps were carried out as described above for other oxazolones, aldehydes and amines, the aldehyde now being quinoline-4-aldehyde.

Example 4

Compounds of formula II with A=4-aminophenyl and N-acetyl-4-aminophenyl; B=1-methylindol-3-yl, naphth-1-yl or quinol-4-yl; and -L-G deriving from (-)-(1R, 2S)-ephedrine.

A1.1. SnCl$_2$ reduction of the ring-opened product of Example 3B1. A=4-aminophenyl; B=1-methylindol-3-yl. The compound obtained in Example 3B1 was reduced with SnCl$_2$.

A1.2. SnCl$_2$ reduction of the ring-opened product of Example 3B2. A=4-aminophenyl; B=naphth-1-yl. The compound obtained in Example 3B2 was reduced with SnCl$_2$.

A1.3. SnCl$_2$ reduction of the ring-opened product from Example 3B3 to its amino analogue. A=4-aminophenyl; B=quinol-4-yl. The compound obtained in Example 3B3 was reduced with SnCl$_2$.

A2. Catalytic reduction of the ring-opened product of Example 3B1. A=4-aminophenyl; B=1-methylindol-3-yl. The compound obtained in Example 3B1 was reduced with H$_2$ on Pd/C. The product was identified to be the same as in Example 4A1.1.

B1. Acylation of an 4-amino phenyl group in part A. The product from Example 4A1.1 was acylated with acetic acid anhydride.

Example 5

Compounds of formula II with A=N-acetyl-4-aminophenyl; B=naphth-1-yl; and -L-G deriving from (-)-(1R,2S)-ephedrine.

A. Introduction of ring systems A and B. This was done by reacting 2-(N-aceto-4-aminophenyl) oxazolone with naphthalene-1-aldehyde.

B. Introduction of the structure -L-G by oxazolone ring opening with (-)-(1R,2S)-ephedrine. This was done in analogy with the above-given procedures and other combinations of oxazolones, aldehydes and amines.

Example 6

Compounds of formula II with A=4-cyanophenyl; B naphth-1-yl; and -L-G deriving from (-)-(1R, 2S)-ephedrine.

A. 2-(4-Cyanophenyl)oxazolone. This compound was obtained from reaction of 4-cyanobenzoyl chloride with glycine to give 4-cyanohippuric acid that subsequently was cyclized with Ac$_2$O.

B. Condensation of 2-(4-cyanophenyl)oxazolone and naphthalene-1-aldehyde. This reaction was carried out in analogy with the procedures given above for other oxazolones and aldehydes.

C. Opening of the oxazolone ring with (-)-(1R, 2S)-ephedrine. The oxazolone product from the preceding step was reacted with the amine as outlined above for other oxazolones.

Example 7

Compounds of formula II with A=4-H$_2$NCO-phenyl; B=naphth-1-yl; and -L-G deriving from (-)-(1R, 2S)-ephedrine.

This product was obtained by hydrolysing the product of Example 6C under oxidative conditions.

Example 8

Compounds of formula II with A=4-aminomethyl-phenyl; B=naphth-1-yl; and -L-G deriving from (-)-(1R, 2S)-ephedrine.

A. Formation of -NHCbz-protected 4-amino hippuric acid. N-Cbz (C$_6$H$_5$CH$_2$OCO—) protected 4-aminomethyl-benzoyl chloride obtained from reaction of N-Cbz protected 4-aminomethyl-benzoic acid with oxalyl chloride was reacted with glycine.

B. Formation of oxazolone. NHCbz protected hippuric acid from step A was cyclisized with dicyclohexyl carbodiimide.

C. Introduction of naphth-1-yl as ring system B and oxazolone ring-opening with (1R,2S)-ephedrine. This was carried out in analogy with the procedures given above for other combinations of oxazolones, aldehydes and amines. The protecting group was removed in the final step.

Example 9

Coupling of a ligand to EAH SEPHAROSE 4B and ECH SEPHAROSE

EAH SEPHAROSE 4B (epoxy activated agarose that has been reacted with 1–6-diamino-hexane) or ECH SEPHAROSE (epoxy activated agarose that has been reacted with 6-amino-hexane carboxyic acid) supplied pre-swollen in 20% ethanol (PHARMACIA BIOTECH AB, Uppsala, Sweden). The ethanol solution was decanted and the gel washed with water on a glass filter. The gel is stepwise washed over into THF. The ligand (100–1501 mol) and dicyclohexyl carbodiimide (200 µmol) is dissolved in THF and is then mixed with 10 ml of the gel (100 µmol amino groups). The suspension is rotated over night (18 h) at room temperature. The gel is washed with 300 ml THF, 300 ml acetone, 300 ml water, 300 ml isopropanol, 300 ml acetonitrile and finally 300 ml water. Remaining groups are blocked with 1.7M acetic acid and 1M dicyclohexyl carbodiimide (DCC) in dioxan. The gel is washed with 150 ml 40° C. isopropanol, 300 ml acetone, 300 ml THF, 300 ml acetonitrile, 300 ml 40° C. isopropanol, 300 ml ethanol and 300 ml water. Finally the gel is washed with alternating high pH (0.1M tris-HCl+0.5M NaCl pH 8.5) and low pH(0.1M NaAcO+0.5M NaCl pH 4.5 with acetic acid) buffers. All together 300 ml high pH buffer and 300 ml low pH buffer were used. The results are given in Table 6.

TABLE 6

Coupled ligands that have affinity to HSA.

| Ligand | | | µmol | µmol |
| --- | --- | --- | --- | --- |
| A-part | B-part | -L-G from | ligand | DCC |
| Thien-2-yl* | Naphth-1-yl | N-methyl-L-Phenylalanine | 100 | 200 |
| Thien-2-yl* | Naphth-1-yl | N-methyl-D-Phenylalanine | 100 | 200 |
| 2-phenyl* | 1-methylindol-3-yl | N-methyl-L-Phenylalanine | 150 | 200 |
| 2-phenyl* | 1-methylindol-3-yl | N-methyl-D-Phenylalanine | 150 | 200 |
| Thien-2-yl* | 1-methylindol-3-yl | N-methyl-L-Phenylalanine | 103 | 200 |
| Thien-2-yl* | 1-methylindol-3-yl | N-methyl-D-Phenylalanine | 97 | 200 |
| 4-aminomethyl phenyl** | Naphth-1-yl | 1R,2S-ephedrine | 200 | 400 |

-L-G indicates that the amino acids indicated have been used for the ring opening of the oxazolone ring. *The final ligand bound to EAH SEPHAROSE. ** The final ligand bound to ECH SEPHAROSE.

We claim:
1. A method for binding albumin, which comprises:
contacting an aqueous liquid containing an albumin with a first compound containing the scaffold —CO—NH—C(=C—)—CO— and having been pre-checked to bind to the albumin, under conditions permitting binding between the albumin and the first compound.

2. The method according to claim 1, wherein said first compound is a ligand in a conjugate having the formula (II):

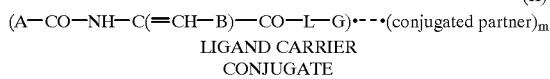

LIGAND CARRIER
CONJUGATE wherein
a. A and B are the same or different and contain a 5- or 6-membered aromatic ring directly attached to the carbonyl, or carbon—carbon-double bond, respectively, of the scaffold;
b. L is a linker —$(CH_2)_n(X)_{m'}(CH_2)_{n'}$—, wherein the left and right free valences bind to the right carbonyl group of the scaffold and to the group G, respectively; X is oxygen, sulphur or NH, with the H of the NH optionally being replaced with a methyl group or a $C_{2-10}$ alkyl group; one or more of the hydrogen atoms in a $CH_2$-group of the linker is optionally replaced with a $C_{1-10}$ alkyl group, or a hydroxy, carboxy or amino group or any group containing a functional group which enables further derivatization and linking to a conjugated partner; n and n' are integers 0–3 and m' is an integer 0 or 1, with the proviso that n+n'+m' is 1, 2 or 3;
c. G is a hydrophobic group;
d. m is 0 or 1;
e. - - - denotes that the conjugated partner, if present, is replacing a hydrogen in the ligand; and
f. conjugated partner is a residue having a molecular weight higher than 118 dalton, and is derived from a second compound.

3. The method of claim 2, wherein n=0, m'=1 and n'=2; X is O or NH with H being substituted with a lower $C_{1-10}$ alkyl; one or more of the hydrogen atoms in a $CH_2$-group of the linker is replaced with a $C_{1-10}$ alkyl group, or a hydroxy, carboxy or amino group.

4. The method of claim 2, wherein one or both of the aromatic rings in A and B comprise one, two or three heteroatoms providing at least one free electron pair and being selected among oxygen, nitrogen or sulphur.

5. The method according to claim 2, wherein each of A and B are represented by the formula:

(III)

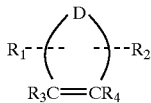

wherein
A) - - - represents that $R_1$ and $R_2$ are substituting $R_3$, $R_4$ or a hydrogen in D;
B) the link from the aromatic ring to the scaffold —CO—NH—C(=CH—)—CO— is through replacement of a hydrogen in D or of one of $R_1$ and $R_2$, or one of $R_3$ and $R_4$;
C) D in formula III is selected from among —NH—CH=CH—, —CH=N—CH—, —NH—CH=N—, —NH—N=CH—, —N=N—NH—, —S—CH=CH—, —O—CH=CH—, —O—CH=N—, —S—CH=N—, —CH=CH—CH=CH—, —CH=CH—CH=N—, —CH=CH—N=CH—, —CH=CH—N=N—, —CH=NH—CH=N—, —N=CH—CH=N—, —N=CH—N=N—, and —N—CH—N=N—;
D) $R_1$ and $R_2$ are selected from the group consisting of:
a. hydrogen (no replacement), alkyl, aryl, alkoxy, aryloxy and their thio analogues, which are optionally substituted;
b. halo;
c. nitro;
d. cyano, carboxamido and carboxy; and
e. amino and corresponding ammonium groups and acylated and alkylated forms thereof,
E) $R_3$ and $R_4$ are hydrogen or together form a bivalent structure selected from among the D structures given above and in addition among —$CH_2$—S—$CH_2$—, —$CH_2$—O—$CH_2$—, —S—$CH_2$—$CH_2$—, —O—$CH_2$—$CH_2$—, —O—CH=CH—$CH_2$—, —$CH_2$—O—CH=CH—, —S—CH=CH—$CH_2$—, —$CH_2$—S—CH=CH—, —S—CH=CH—NH—, —$CH_2$—$CH_2$—$CH_2$—, —$CH_2$—$CH_2$—$CH_2$—$CH_2$—, —$CH_2$—CH=CH—, —$CH_2$CH=CH—$CH_2$—, and —$CH_2$—$CH_2$—CH=CH—.

6. The method of claim 2, wherein one or both of the aromatic rings are selected from the group consisting of phenyls, 1- and 2-naphthyls, 1- and 2-thienyls, 2-, 3- and 4-pyridyls, 2-, 3- and 4-quinolyls, 1-, 3- and 4-isoquinolyls, 2- and 3-indolyls, 2- and 3-furanyls, and 1-, 2- and 3-pyrrolyls.

7. The method of claim 2, wherein G is an aryl group or an aryl group that is substituted with hydroxy and/or $C_{1-10}$ alkyl in the ortho, meta or para position relative to the ring position binding to L.

8. The method of claim 2, wherein m =1 and the conjugated partner is selected from polymeric carriers or analytically detectable carriers.

9. The method of claim 2, wherein the conjugated partner is linked to the ligand at either the A-, B-, or L-parts.

10. The method of claim 2, wherein the conjugated partner is attached at either the A- or the B-part and the conjugated partner provides an sp³-hybridized atom within two atoms distance from the aromatic ring in the A-part or B-part to which attachment occurs.

11. The method of claim 10, wherein the conjugated partner provides the group —$CH_2$—$CH_2$—, —$CH_2NH$—, —$NHCH_2$—, —$CH_2O$—, or —$OCH_2$— next to the aromatic ring.

12. The method of claim 9, wherein the conjugated partner is linked to L at a —CONH— or —COO— group substituting a hydrogen in L.

13. The method of claim 12, wherein n=0, n'=2, m'=1, X=O or NH, with H in the NH optionally being substituted with a lower $C_{1-10}$ alkyl.

14. The method of claim 2, wherein the conjugated partner is a support matrix for affinity adsorption.

15. A conjugate having the structure of formula II:

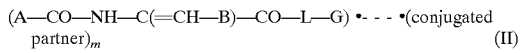

wherein A, B, and G and - - - are as defined in claim 2; m=1, wherein the conjugated partner is linked to the ligand either at the A-, B-, or L-part.

16. The conjugate of claim 15, wherein the conjugated partner is attached to the ligand at the aromatic ring of either the A- or the B-part and the conjugated partner provides an sp³-hybridized carbon atom within a distance of two atoms from the aromatic ring of the A- or the B-part to which the attachment occurs.

17. The conjugate of claim 16, wherein the conjugated partner provides —$CH_2$—$CH_2$—, —$CH_2NH$—, —$NHCH_2$—, —$CH_2O$—, or —$OCH_2$— next to the aromatic ring.

18. The conjugate of claim 15, wherein the conjugated partner is linked to L at a —CONH— or —COO— group substituting a hydrogen in L.

19. The conjugate of claim 15, wherein n=0, n'=2, m'=1, X=O or NH, with H in the NH optionally being replaced by a lower $C_{1-10}$ alkyl.

20. The conjugate of claim 15, wherein the conjugated partner is a support matrix for affinity adsorption.

21. The method of claim 2, wherein a hydrogen in NH of L is replaced with a methyl group or a $C_{2-10}$ alkyl group.

22. The method of claim 5, wherein said groups $R_1$ and $R_2$ are substituted with at least one halo group.

23. The method of claim 22, wherein $R_1$ and $R_2$ are $C_{1-10}$ alkyl or $C_{5-15}$ aryl group, optionally substituted with one or more lower alkyl or halo groups.

24. The method of claim 22, wherein $R_1$ and $R_2$ are phenyl.

25. The method of claim 13, wherein a hydrogen in NH of L is replaced with a methyl group or a $C_{2-10}$ alkyl group.

26. The method of claim 14, wherein said support matrix is a chromatographic support matrix.

27. The conjugate of claim 20, wherein said support matrix is a chromatographic support matrix.

28. The method according to claim 5, wherein in part (D)(e), said amino group is a primary, secondary or tertiary amino group, and said ammonium group is quaternary ammonium group.

29. The method according to claim 23, wherein $R_1$ and $R_2$ are selected from the group consisting of methyl, phenyl and $CF_3$.

30. A method for binding albumin, which comprises:
contacting an aqueous liquid containing an albumin with an albumin-binding first compound containing the scaffold —CO—NH—C(=CH—)—CO— under conditions permitting binding between the albumin and the albumin-binding first compound, and separating bound albumin from the liquid.

31. The method of claim 30, wherein said first compound is a ligand in a conjugate having the formula (II):

$$(A-CO-NH-C(=CH-B)-CO-L-G)\cdots\cdot(\text{conjugated partner})_m \quad (II)$$
LIGAND CARRIER CONJUGATE wherein
a. A and B are the same or different and contain a 5- or 6-membered aromatic ring directly attached to the carbonyl or carbon-carbon-double bond, respectively, of the scaffold;
b. L is a linker —$(CH_2)_n(X)_{m'}(CH_2)_{n'}$—, wherein the left and right free valences bind to the right carbonyl group of the scaffold and to the group G, respectively; X is oxygen, sulphur or NH, with the H of the NH optionally being replaced with a methyl group or a $C_{2-10}$ alkyl group; one or more of the hydrogen atoms in a $CH_2$-group of the linker is optionally replaced with a $C_{1-10}$ alkyl group, or a hydroxy, carboxy or amino group or any group containing a functional group which enables further derivatization and linking to a conjugated partner; n and n' are integers 0–3 and m' is an integer C or 1, with the proviso that n+n'+m' is 1, 2 or 3;
c. G is a hydrophobic group;
d. m is 0 or 1;
e. - - - denotes that the conjugated partner, if present, is replacing a hydrogen in the ligand; and
f. conjugated partner is a residue having a molecular weight higher than 118 dalton, and is derived from a compound.

32. The method of claim 31, wherein n=0, m=1 and n'=2; X is O or NH with H being substituted with a lower $C_{1-10}$ alkyl; one or more of the hydrogen atoms in a $CH_2$-group of the linker is replaced with a $C_{1-10}$ alkyl group, or a hydroxy, carboxy or amino group.

33. The method of claim 31, wherein one or both of the aromatic rings in A and B comprise one, two or three heteroatoms providing at least one free electron pair and being selected from among oxygen, nitrogen and sulphur.

34. The method according to claim 31, wherein each of A and B is represented by the formula:

$$R_1-\left(\begin{array}{c}D\\ \\R_3C=CR_4\end{array}\right)-R_2 \quad (III)$$

wherein
A) - - - represents that $R_1$ and $R_2$ are substituting $R_3$, $R_4$ or a hydrogen in D;
B) the link from the aromatic ring to the scaffold —CO—NH—C(=CH—)—CO— is through replacement of a hydrogen in D or of one of $R_1$ and $R_2$, or one of $R_3$ and $R_4$;
C) D in formula III is selected from among —NH—CH=CH—, —CH=N—CH—, —NH—CH=N—, —NH—N=CH—, —N=N—NH—, —S—CH=CH—, —O—CH=CH—, —O—CH=N—, —S—CH=N—, —CH=CH—CH=CH—, —CH=CH—CH=N—, —CH=CH—N=CH—, —CH=CH—N=N—, —CH=NH—CH=N—, —N=CH—CH=N—, —N=CH—N=N—, and —N=CH—N=N—;
D) $R_1$ and $R_2$ are selected from the group consisting of:
a. hydrogen (no replacement), alkyl, aryl, alkoxy, aryloxy and their thio analogues, which are optionally substituted;
b. halo;
c. nitro;
d. cyano, carboxamido and carboxy; and
e. amino and corresponding ammonium groups and acylated and alkylated forms thereof,
E) $R_3$ and $R_4$ are hydrogen or together form a bivalent structure selected from among the D structures given above and in addition among —$CH_2$—S—$CH_2$, —$CH_2$—O—$CH_2$—, —S—$CH_2$—$CH_2$—, —O—$CH_2$—$CH_2$—, —O—CH=CH—$CH_2$—, —$CH_2$—O—CH=CH—, —S—CH=CH—$CH_2$—, —$CH_2$—S—CH=CH—, —S—CH=CH—NH—, —$CH_2$—$CH_2$—$CH_2$—, —$CH_2$—$CH_2$—$CH_2$—$CH_2$—, —$CH_2$—CH=CH—, —$CH_2$CH=CH—$CH_2$—, and —$CH_2$—$CH_2$—CH=CH.

35. The method of claim 31, wherein the conjugated partner is a support matrix for affinity adsorption.

36. The method of claim 35, wherein said support matrix is a chromatographic support matrix.

* * * * *